US012583847B2

(12) United States Patent
Seino et al.

(10) Patent No.: US 12,583,847 B2
(45) Date of Patent: Mar. 24, 2026

(54) FLUORINATED PYRIMIDINE COMPOUND AND METHOD FOR PRODUCING SAME

(71) Applicant: UNIMATEC CO., LTD., Tokyo (JP)

(72) Inventors: Junya Seino, Kitaibaraki (JP); Rie Aotsu, Kitaibaraki (JP); Keisuke Kokin, Kitaibaraki (JP)

(73) Assignee: UNIMATEC CO., LTD. (JP)

( * ) Notice: Subject to any disclaimer, the term of this patent is extended or adjusted under 35 U.S.C. 154(b) by 346 days.

(21) Appl. No.: 18/282,718

(22) PCT Filed: Mar. 16, 2022

(86) PCT No.: PCT/JP2022/011917

§ 371 (c)(1),
(2) Date: Sep. 18, 2023

(87) PCT Pub. No.: WO2022/202537

PCT Pub. Date: Sep. 29, 2022

(65) Prior Publication Data

US 2024/0190853 A1 Jun. 13, 2024

(30) Foreign Application Priority Data

Mar. 22, 2021 (JP) ................................. 2021-047661

(51) Int. Cl.
*C07D 413/04* (2006.01)

(52) U.S. Cl.
CPC .................................. *C07D 413/04* (2013.01)

(58) Field of Classification Search
CPC .................................................... C07D 413/04
USPC .......................................................... 544/333
See application file for complete search history.

(56) References Cited

U.S. PATENT DOCUMENTS

2021/0403455 A1 12/2021 Seino et al.

FOREIGN PATENT DOCUMENTS

| | | | |
|---|---|---|---|
| EP | 4059927 | A1 | 9/2022 |
| JP | S59-104364 | A | 6/1984 |
| JP | S63-216877 | A | 9/1988 |
| WO | 2015-085909 | A1 | 6/2015 |
| WO | 2019-007140 | A1 | 1/2019 |
| WO | 2020-116296 | A1 | 6/2020 |
| WO | 2021-095577 | A1 | 5/2021 |

OTHER PUBLICATIONS

Office Action issued in corresponding India Patent Application No. 202337062092 dated Apr. 12, 2024, with English translation (6 Pages).
The First Office Action for corresponding Chinese Patent Application No. 202280021436.1 dated Jul. 29, 2025, with English translation (14 Pages).
International Search Report for corresponding International Application No. PCT/JP2022/011917 dated May 31, 2022, with English translation (5 Pages).
Written Opinion for corresponding International Application No. PCT/JP2022/011917 dated May 31, 2022, with English translation (6 Pages).
International Preliminary Report on Patentability for corresponding International Application No. PCT/JP2022/011917 dated May 31, 2022, with English translation (7 Pages).
Extended European Search Report for corresponding European Patent Application No. 22775325.8 dated Feb. 6, 2025 (6 Pages).
Notice of Reasons for Refusal for corresponding Japanese Patent Application No. 2023-509065 dated Sep. 24, 2024, with English translation (6 Pages).

(Continued)

*Primary Examiner* — Kristin A Vajda
(74) *Attorney, Agent, or Firm* — Harness, Dickey & Pierce, P.L.C.

(57) ABSTRACT

A fluorinated pyrimidine compound represented by the following general formula (1a) or (1b):

(1a)

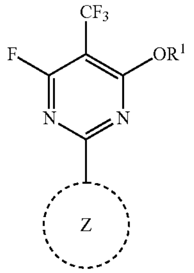

(1b)

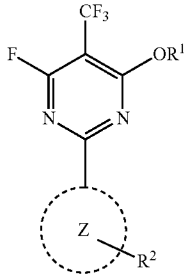

wherein $R^1$ represents a hydrocarbon group having 1 to 12 carbon atoms, $R^2$ represents a halogen atom, a hydrocarbon group having 1 to 10 carbon atoms, $—C_nF_{2n+1}$, a nitro group, a boronic acid group, a cyano group, $—OA^1$, $—O_l-SO_mA^1$, $—NA^1A^2$, $—O_lCOOA^1$, or $—O_lCONA^1A^2$, $A^1$ and $A^2$ each independently represent a hydrogen atom or a hydrocarbon group having 1 to 10 carbon atoms, $A^1$ and $A^2$ may be bonded to form a ring structure, and when a plurality of $R^2$ is present, the plurality of $R^2$ may be the same or different from each other, and a ring Z is a 5-membered aromatic heterocyclic ring containing one oxygen atom and one or more nitrogen atoms.

6 Claims, No Drawings

(56) References Cited

OTHER PUBLICATIONS

Inouye, Yoshio. et al., "A Facile One-Pot Preparation of 2-Methyl- and 2-Phenyl-4-fluoro-5-trifluoromethyl-6-methoxypyrimidin from Methyl 2-hydryl-2-(F-methyl) F-propyl Ether", Journal of Fluorine Chemistry, 1985, 27, pp. 231-236 (6 Pages).
Rejection Decision for corresponding Chinese Patent Application No. 202280021436.1 dated Nov. 13, 2025, with English translation (14 Pages).

FLUORINATED PYRIMIDINE COMPOUND AND METHOD FOR PRODUCING SAME

CROSS REFERENCE TO RELATED APPLICATIONS

The present application is a national stage application of International Patent Application No. PCT/JP2022/011917 filed on Mar. 16, 2022, which claims the benefit of Japanese Patent Application No. 2021-047661, filed on Mar. 22, 2021. The contents of the above applications are incorporated herein by reference in their entirety.

BACKGROUND

Technical Field

The present disclosure relates to a fluorinated pyrimidine compound and a method for producing the same.

Related Art

Conventionally, fluorinated pyrimidine compounds have been reported to have various biological activities. Among them, a compound having an aromatic heterocyclic ring containing a nitrogen atom and an oxygen atom as a substituent at the 2-position of a pyrimidine ring and a fluorinated substituent at the 5-position of the pyrimidine ring is expected to be used in the fields of medicine and agrochemicals. WO2019/007140 discloses a compound having an oxazole ring substituent at the 2-position of a pyrimidine ring, an amino group at the 4-position of a pyrimidine ring, and a heteroatom or heteroatom-containing substituent at the 6-position of a pyrimidine ring, and a trifluoromethyl group at the 5-position of a pyrimidine ring, and that the compound has adenosine A2a receptor antagonist activity.

SUMMARY OF DISCLOSURE

Technical Problem

However, a novel fluorinated pyrimidine compound that has a trifluoromethyl group at the 5-position of a pyrimidine ring, an oxygen-containing substituent at the 4-position of a pyrimidine ring, and a fluorine atom at the 6-position of a pyrimidine ring, has been demanded in anticipation of further improvement in biological activity. Moreover, a one-step production method capable of easily producing such a fluorinated pyrimidine compound has been desired.

The present disclosure was made in view of the aforementioned circumstances. Namely, the present inventors have found that a unique aromatic heterocyclic ring structure can be introduced at the 2-position between two nitrogen atoms on a pyrimidine ring having specific substituents at the 4-, 5-, and 6-positions by reacting specific raw materials, and thus have completed the present disclosure. Provided are a novel fluorinated pyrimidine compound that has a trifluoromethyl group at the 5-position of the pyrimidine ring, an oxygen-containing substituent at the 4-position of the pyrimidine ring, and a fluorine atom at the 6-position of the pyrimidine ring, and a nitrogen and oxygen-containing aromatic heterocyclic ring at the 2-position of the pyrimidine ring as a substituent, and a production method capable of easily producing the fluorinated pyrimidine compound.

SUMMARY

The gist of the composition of the present disclosure is as follows.

[1] A fluorinated pyrimidine compound represented by the following general formula (1a) or (1b):

[Formula 1]

(1a)

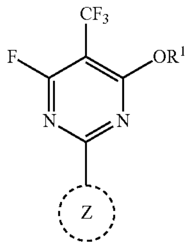

(1b)

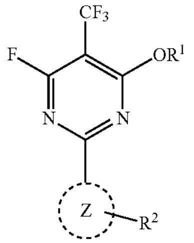

wherein $R^1$ represents a hydrocarbon group having 1 to 12 carbon atoms, $R^2$ represents a halogen atom, a hydrocarbon group having 1 to 10 carbon atoms, $-CnF_{2n+1}$ where n is an integer of 1 to 10, a nitro group, a boronic acid group, a cyano group, $-OA^1$, $-O_lSO_mA^1$ where l is an integer of 0 to 1 and m is an integer of 0 to 3, $-NA^1A^2$, $-O_lCOOA^1$ where l is an integer of 0 to 1, or $-O_lCONA^1A^2$ where l is an integer of 0 to 1, $A^1$ and $A^2$ each independently represent a hydrogen atom or a hydrocarbon group having 1 to 10 carbon atoms, $A^1$ and $A^2$ may be bonded to form a ring structure, and when a plurality of $R^2$ is present, the plurality of $R^2$ is the same or different from each other, and a ring Z is a 5-membered aromatic heterocyclic ring containing one oxygen atom and one or more nitrogen atoms.

[2] The fluorinated pyrimidine compound according to [1] above, wherein the ring Z has a structure of any one of the following formulae (c1) to (c14):

[Formula 2]

(c1)

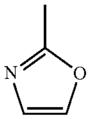

(c2)

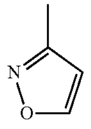

(c3)

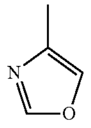

-continued (c4)

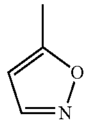

(c5)

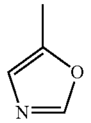

(c6)

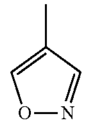

(c7)

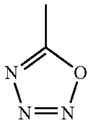

(c8)

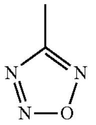

(c9)

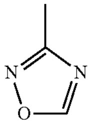

(c10)

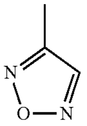

(c11)

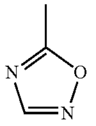

(c12)

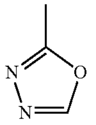

(c13)

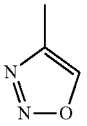

(c14)

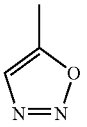

[3] A method for producing a fluorinated pyrimidine compound, including reacting a fluoroisobutylene derivative represented by the following general formula (2) with a compound represented by the following general formula (3a) or a salt thereof to obtain a fluorinated pyrimidine compound represented by the following general formula (1a), or reacting a fluoroisobutylene derivative represented by the following general formula (2) with a compound represented by the following general formula (3b) or a salt thereof to obtain a fluorinated pyrimidine compound represented by the following general formula (1b):

[Formula 3]

(2)

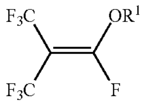

(3a)

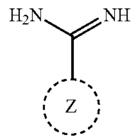

(1a)

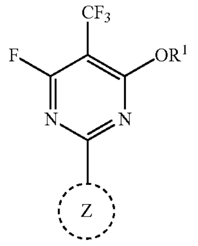

(2)

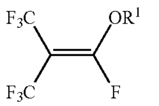

(3b)

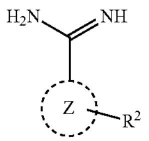

(1b)

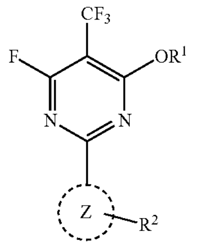

wherein $R^1$ represents a hydrocarbon group having 1 to 12 carbon atoms, $R^2$ represents a halogen atom, a hydrocarbon group having 1 to 10 carbon atoms, $—C_nF_{2n+1}$ where n is an integer of 1 to 10, a nitro group, a boronic acid group, a cyano group, $—OA^1$, $—O_1SO_mA^1$ where 1 is an integer of 0 to 1 and m is an integer of 0 to 3, $—NA^1A^2$, $—O_1COOA^1$ where 1 is an integer of 0 to 1, or $—O_1CONA^1A^2$ where 1 is an integer of 0 to 1, $A^1$ and $A^2$ each independently represent a hydrogen atom or a hydrocarbon group having 1 to 10 carbon atoms, $A^1$ and $A^2$ may be bonded to form a ring structure, and when a plurality of $R^2$ is present, the plurality of $R^2$ is the same or different from each other, and a ring Z is a 5-membered aromatic heterocyclic ring containing one oxygen atom and one or more nitrogen atoms.

[4] A method for producing a fluorinated pyrimidine compound, including reacting a fluoroisobutane derivative represented by the following general formula (4) with a compound represented by the following general formula (3a) or a salt thereof to obtain a fluorinated pyrimidine compound represented by the following general formula (1a), or reacting a fluoroisobutane derivative represented by the following general formula (4) with a compound represented by the following general formula (3b) or a salt thereof to obtain a fluorinated pyrimidine compound represented by the following general formula (1b):

[Formula 4]

(4)

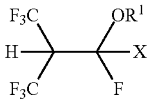

(3a)

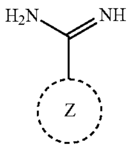

(1a)

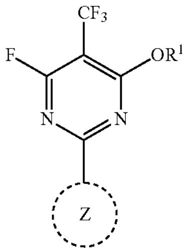

(4)

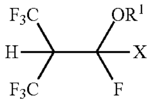

(3b)

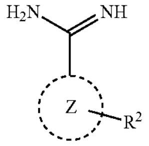

(1b)

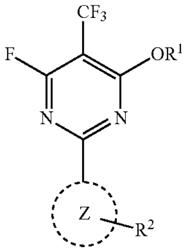

wherein $R^1$ represents a hydrocarbon group having 1 to 12 carbon atoms, $R^2$ represents a halogen atom, a hydrocarbon group having 1 to 10 carbon atoms, $—C_nF_{2n+1}$ where n is an integer of 1 to 10, a nitro group, a boronic acid group, a cyano group, $—OA^1$, $—O_lSO_mA^1$ where l is an integer of 0 to 1 and m is an integer of 0 to 3, $—NA^1A^2$, $—O_lCOOA^1$ where l is an integer of 0 to 1, or $—O_lCONA^1A^2$ where l is an integer of 0 to 1, $A^1$ and $A^2$ each independently represent a hydrogen atom or a hydrocarbon group having 1 to 10 carbon atoms, $A^1$ and $A^2$ may be bonded to form a ring structure, and when a plurality of $R^2$ is present, the plurality of $R^2$ is the same or different from each other, a ring Z is a 5-membered aromatic heterocyclic ring containing one oxygen atom and one or more nitrogen atoms, and X represents a halogen atom, a cyano group, $—OA^3$, $—NA^3A^4$, $—OCOOA^3$, $—OCONA^3A^4$, or $—O_lSO_mA^5$ where l is an integer of 0 to 1 and m is an integer of 0 to 3, $A^3$ and $A^4$ each independently represent a hydrocarbon group having 1 to 10 carbon atoms, $A^3$ and $A^4$ may be bonded to form a ring structure, and $A^5$ represents a hydrogen atom or a hydrocarbon group having 1 to 10 carbon atoms.

[5] The method for producing a fluorinated pyrimidine compound according to [3] above, wherein the ring Z has a structure of any one of the following formulae (c1) to (c14):

[Formula 5]

(c1)

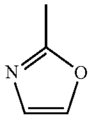

(c2)

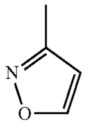

(c3)

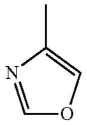

(c4)

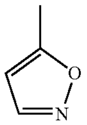

(c5)

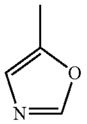

(c6)

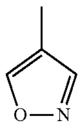

-continued
(c7)
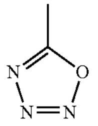
(c8)
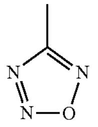
(c9)
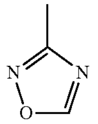
(c10)
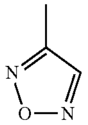
(c11)
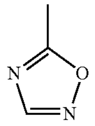
(c12)
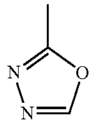
(c13)
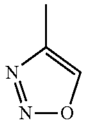
(c14)
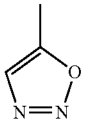
[6] The method for producing a fluorinated pyrimidine compound according to [4] above, wherein the ring Z has a structure of any one of the following formulae (c1) to (c14):
[Formula 6]
(c1)
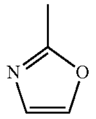
(c2)
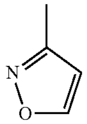
-continued
(c3)
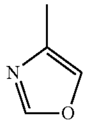
(c4)
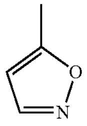
(c5)
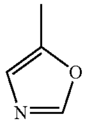
(c6)
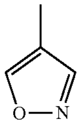
(c7)
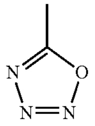
(c8)
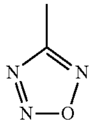
(c9)
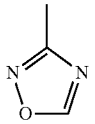
(c10)
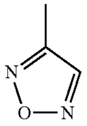
(c11)
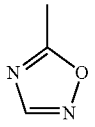
(c12)
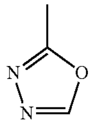
(c13)
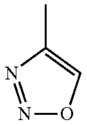

-continued (c14)

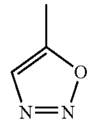

Effects of Disclosure

It is possible to provide a novel fluorinated pyrimidine compound that has a trifluoromethyl group at the 5-position of the pyrimidine ring, an oxygen-containing substituent at the 4-position of the pyrimidine ring, and a fluorine atom at the 6-position of the pyrimidine ring, and a nitrogen and oxygen-containing aromatic heterocyclic ring at the 2-position of the pyrimidine ring as a substituent, and a production method capable of easily producing the fluorinated pyrimidine compound.

DETAILED DESCRIPTION

Fluorinated Pyrimidine Compound

The fluorinated pyrimidine compound of one embodiment is represented by the following general formula (1a) or (1b).

[Formula 7]

(1a)

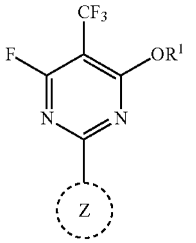

(1b)

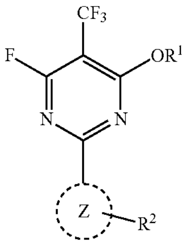

wherein $R^1$ represents a hydrocarbon group having 1 to 12 carbon atoms, $R^2$ represents a halogen atom, a hydrocarbon group having 1 to 10 carbon atoms, $—C_nF_{2n+1}$ where n is an integer of 1 to 10, a nitro group, a boronic acid group, a cyano group, $—OA^1$, $—O_lSO_mA^1$ where l is an integer of 0 to 1 and m is an integer of 0 to 3, $—NA^1A^2$, $—O_lCOOA^1$ where l is an integer of 0 to 1, or $—O_lCONA^1A^2$ where l is an integer of 0 to 1, $A^1$ and $A^2$ each independently represent a hydrogen atom or a hydrocarbon group having 1 to 10 carbon atoms, $A^1$ and $A^2$ may be bonded to form a ring structure, and when a plurality of $R^2$ is present, the plurality of $R^2$ may be the same or different from each other, and a ring Z is a 5-membered aromatic heterocyclic ring containing one oxygen atom and one or more nitrogen atoms.

The ring Z is composed of five ring atoms and is not particularly limited as long as the ring Z is a 5-membered aromatic heterocyclic ring containing one oxygen atom and one or more nitrogen atoms as ring atoms. The number of nitrogen atoms as ring atoms is one or more, and for example, the number of nitrogen atoms can be one, two, or three. The ring Z may also contain a heteroatom other than an oxygen atom and a nitrogen atom as a ring atom. Examples of such a heteroatom include a sulfur atom. The ring Z may have a substituent or may not have a substituent in some cases.

Examples of the ring Z can include groups having structures represented by the following formulae (c1) to (c14). The structures of the following formulae (c1) to (c14) may be further bonded with $R^2$ as a substituent.

[Formula 8]

(c1)

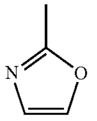

(c2)

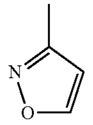

(c3)

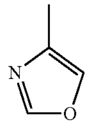

(c4)

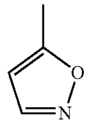

(c5)

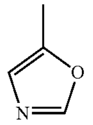

(c6)

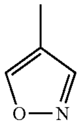

(c7)

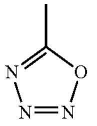

(c8)

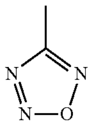

-continued (c9)

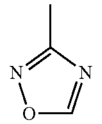

(c10)

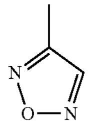

(c11)

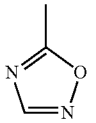

(c12)

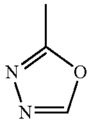

(c13)

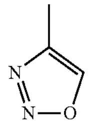

(c14)

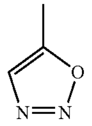

$R^1$ is not particularly limited as long as it is a hydrocarbon group having 1 to 12 carbon atoms and is composed of a carbon atom and a hydrogen atom, and includes a chain hydrocarbon group, an aromatic hydrocarbon group, an alicyclic hydrocarbon group and the like. The chain hydrocarbon group is not particularly limited as long as the total number of carbon atoms is 1 to 12, and may be a branched chain hydrocarbon group or an unbranched chain hydrocarbon group. The aromatic hydrocarbon group is not particularly limited as long as the total number of carbon atoms is 1 to 12, and may be an aromatic hydrocarbon group having a substituent or an aromatic hydrocarbon group having no substituent. Moreover, the aromatic hydrocarbon group may have a condensed polycyclic structure. The alicyclic hydrocarbon group is not particularly limited as long as the total number of carbon atoms is 1 to 12, and may be an alicyclic hydrocarbon group having a substituent or an alicyclic hydrocarbon group having no substituent. Further, the alicyclic hydrocarbon group may have a bridged ring structure.

Examples of the chain hydrocarbon group include alkyl groups such as a methyl group, an ethyl group, a n-propyl group, an i-propyl group, a n-butyl group, an i-butyl group, a sec-butyl group, a t-butyl group, a pentyl group, a hexyl group, a heptyl group, an octyl group, a nonyl group, a decyl group, an undecyl group and a dodecyl group;

alkenyl groups such as an ethenyl group, a propenyl group, a butenyl group, a pentenyl group, a hexenyl group, a heptenyl group, an octenyl group, a nonenyl group, a decenyl group, an undecenyl group and a dodecenyl group; and alkynyl groups such as an ethynyl group, a propynyl group, a butynyl group, a pentynyl group, a hexynyl group, a heptynyl group, an octynyl group, a nonynyl group, a decynyl group, an undecynyl group and a dodecynyl group.

Examples of the aromatic hydrocarbon group include a phenyl group and a naphthyl group.

Examples of the alicyclic hydrocarbon group include a saturated or unsaturated cyclic hydrocarbon group, and examples of the cyclic hydrocarbon group include a cyclopropyl group, a cyclobutyl group, a cyclohexyl group, a cyclopentyl group, an adamantyl group and a norbornyl group.

$R^1$ is preferably an alkyl group having 1 to 10 carbon atoms. $R^1$ being an alkyl group having 1 to 10 carbon atoms enables the fluoroisobutylene derivative of the general formula (2) and the fluoroisobutane derivative of the general formula (4), which are raw materials of the fluorinated pyrimidine compound, to be easily prepared.

In the fluorinated pyrimidine compound of the general formula (1b), one $R^2$ may be present, or a plurality of $R^2$ may be present. When a plurality of $R^2$ is present, the plurality of $R^2$ may be the same or different from each other. Examples of a halogen atom that is $R^2$ can include F, Cl, Br, and I. A hydrocarbon group having 1 to 10 carbon atoms that is $R^2$ can be a hydrocarbon group having 1 to 10 carbon atoms in $R^1$ described above. $R^2$ may also be $—C_nF_{2n+1}$ where n is an integer of 1 to 10, a nitro group ($—NO_2$), a boronic acid group ($—B(OH)_2$), or a cyano group (—CN).

$A^1$ included in $—OA^1$ and $—O_lSO_mA^1$ where l is an integer of 0 to 1 and m is an integer of 0 to 3, which are $R^2$, represents a hydrogen atom or a hydrocarbon group having 1 to 10 carbon atoms. $A^1$ and $A^2$ included in $—NA^1A^2$ that is $R^2$ each independently represent a hydrogen atom or a hydrocarbon group having 1 to 10 carbon atoms, and $A^1$ and $A^2$ a may be bonded to form a ring structure. Examples of groups of the ring structure formed by bonding of $A^1$ and $A^2$ that are included in $—NA^1A^2$ can include a pyrrolidinyl group, a piperidinyl group, and a morpholinyl group. When $A^1$ and $A^2$ each represent a hydrocarbon group having 1 to 10 carbon atoms, for example, it can be a hydrocarbon group having 1 to 10 carbon atoms in $R^1$ described above.

$A^1$ included in $—O_lCOOA^1$ where l is an integer of 0 to 1, which is $R^2$, represents a hydrogen atom or a hydrocarbon group having 1 to 10 carbon atoms. When $A^1$ represents a hydrocarbon group having 1 to 10 carbon atoms, for example, it can be a hydrocarbon group having 1 to 10 carbon atoms in $R^1$ described above.

$A^1$ and $A^2$ included in $—O_lCONA^1A^2$ where l is an integer of 0 to 1, which is $R^2$, each independently represent a hydrogen atom or a hydrocarbon group having 1 to 10 carbon atoms, and $A^1$ and $A^2$ may be bonded to form a ring structure. Examples of groups of the ring structure formed by bonding of $A^1$ and $A^2$ in $NA^1A^2$ included in $—O_lCONA^1A^2$ can include a pyrrolidinyl group, a piperidinyl group, and a morpholinyl group. When $A^1$ and $A^2$ each represent a hydrocarbon group having 1 to 10 carbon atoms, for example, it can be a hydrocarbon group having 1 to 10 carbon atoms in $R^1$ described above.

The fluorinated pyrimidine compound of one embodiment has a specific substituent at the 2-position of the pyrimidine ring (5-membered aromatic heterocyclic ring containing one oxygen atom and one or more nitrogen atoms), and specific substituents on the 4-position, 5-position, and 6-position of the pyrimidine ring ($—OR^1$, $—CF_3$, and —F), and thereby it can have an excellent effect from the viewpoint of structural expandability. In particular, desired biological activity (for example, hormone or enzyme inhibitory activity, fungicidal activity, insecticidal activity, and herbicidal activity)

can be expected. Having a specific substituent on the 2-position of the pyrimidine ring can impart further properties to the fluorinated pyrimidine compound of one embodiment. Moreover, the substituents on the 4- and 6-positions of the pyrimidine ring being different groups (—$OR^1$ and —F) can facilitate derivatization into an asymmetric structure, which can also be expected to be used as an intermediate. More specifically, reacting the fluorinated pyrimidine compound under acidic conditions to modify —$OR^1$ can provide a derivative. Moreover, reacting the fluorinated pyrimidine compound under basic conditions to modify —F can provide a derivative. The fluorinated pyrimidine compound of one embodiment is useful in the field of, for example, electronic materials such as organic semiconductors and liquid crystals.

Method for Producing Fluorinated Pyrimidine Compound

The method for producing a fluorinated pyrimidine compound of one embodiment includes:

(a) reacting a fluoroisobutylene derivative represented by the following general formula (2) with a compound represented by the following general formula (3a) or a salt thereof to obtain a fluorinated pyrimidine compound represented by the following general formula (1a), or reacting a fluoroisobutylene derivative represented by the following general formula (2) with a compound represented by the following general formula (3b) or a salt thereof to obtain a fluorinated pyrimidine compound represented by the following general formula (1b):

[Formula 9]

(2)

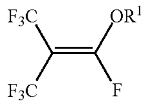

(3a)

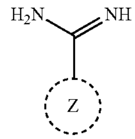

(1a)

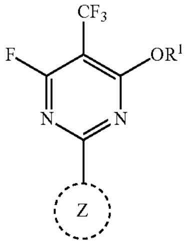

(2)

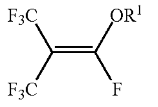

(3b)

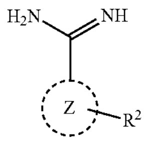

-continued (1b)

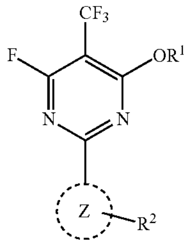

wherein $R^1$ represents a hydrocarbon group having 1 to 12 carbon atoms, $R^2$ represents a halogen atom, a hydrocarbon group having 1 to 10 carbon atoms, —$C_nF_{2n+1}$ where n is an integer of 1 to 10, a nitro group, a boronic acid group, a cyano group, —$OA^1$, —$O_lSO_mA^1$ where l is an integer of 0 to 1 and m is an integer of 0 to 3, —$NA^1A^2$, —$O_lCOOA^1$ where l is an integer of 0 to 1, or —$O_lCONA^1A^2$ where l is an integer of 0 to 1, $A^1$ and $A^2$ each independently represent a hydrogen atom or a hydrocarbon group having 1 to 10 carbon atoms, $A^1$ and $A^2$ may be bonded to form a ring structure, and when a plurality of $R^2$ is present, the plurality of $R^2$ may be the same or different from each other, and a ring Z is a 5-membered aromatic heterocyclic ring containing one oxygen atom and one or more nitrogen atoms.

$R^1$, $R^2$, $A^1$, $A^2$, and the ring Z in the compounds of the general formulae (2), (3a), and (3b) in step (a) above can be specifically the same as $R^1$, $R^2$, $A^1$, $A^2$, and the ring Z in the compounds of the general formulae (1a) and (1b). Examples of the ring Z can include groups having structures represented by the following formulae (c1) to (c14). The structures of the following formulae (c1) to (c14) may be further bonded with $R^2$ as a substituent.

[Formula 10]

(c1)

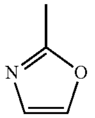

(c2)

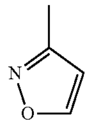

(c3)

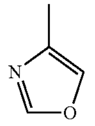

(c4)

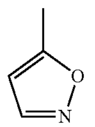

-continued (c5)

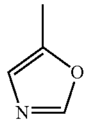

(c6)

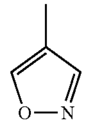

(c7)

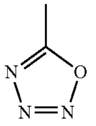

(c8)

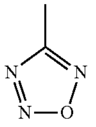

(c9)

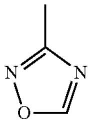

(c10)

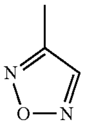

(c11)

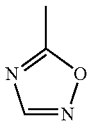

(c12)

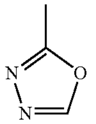

(c13)

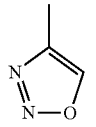

(c14)

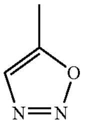

$R^1$ in the above general formulae (1a), (1b), and (2) each preferably represent an alkyl group having 1 to 10 carbon atoms.

The reaction of (a) above of the fluoroisobutylene derivative represented by the general formula (2) and the compound represented by the general formula (3a) or (3b) is represented as the following reaction formula (A)

[Formula 11]

(A)

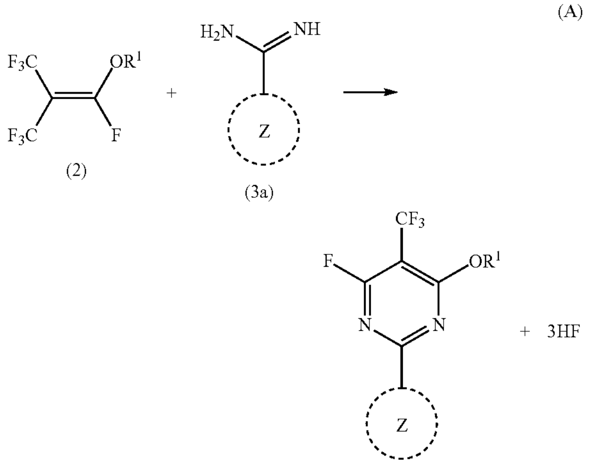

(2) (3a) (1a)

(A)

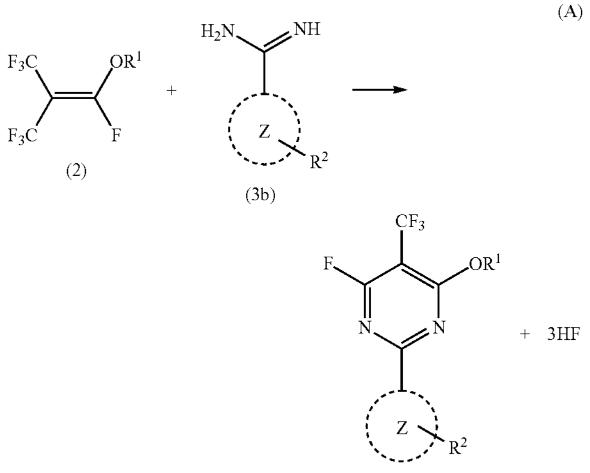

(2) (3b) (1b)

In the above reaction formula (A), the compounds of the general formulae (3a) and (3b) may be in the form of salts. Examples of the compounds of the general formulae (3a) and (3b) in the form of salts include a compound in a form of at least one moiety of the amino moiety ($-NH_2$) and the imino moiety ($=NH$) constituting the amidino group of the compounds of the general formulae (3a) and (3b), being cationized to ($-NH_3^+$) and ($=NH_2^+$) respectively, to form a salt with the counterion. The counterion is not particularly limited as long as it is a monovalent anion, and includes, for example, halide ions such as $F^-$, $Cl^-$, $Br^-$ and $I^-$.

In the method for producing a fluorinated pyrimidine compound of one embodiment, for example, the reaction of (a) above can be carried out in one step in the presence of a hydrogen halide scavenger. Therefore, the fluorinated pyrimidine compound of the above general formula (1a) or (1b) can be easily obtained. In the reaction of (a) above, a cyclic pyrimidine structure is formed between the fluoroisobutylene derivative and the amidino group of the compound of the general formula (3a) or (3b). At the 2-position of the pyrimidine structure, a group derived from the ring structure Z in the compound of the general formula (3a) or (3b) is located. Further, $-OR^1$, $CF_3$ and F derived from the fluoroisobutylene derivative are located at the 4-position, 5-position and 6-position of the pyrimidine structure, respectively.

The hydrogen halide scavenger is a substance having a function of capturing hydrogen fluoride (HF) formed from a hydrogen atom derived from the amidino group in the compounds of the general formula (3a) or (3b) and a fluorine atom derived from the fluoroisobutylene derivative of the general formula (2), in the above reaction formula (A). As the hydrogen halide scavenger, sodium hydroxide, potassium hydroxide, calcium hydroxide, sodium carbonate, potassium carbonate, sodium fluoride and potassium fluoride, and an organic nitrogen derivative such as pyridine, triethylamine, diisopropylethylamine, diazabicyclononene, diazabicycloundecene, methyltriazabicyclodecene and diazabicyclooctane, can be used.

A reaction temperature upon reaction (a) above is preferably 0 to 100° C., more preferably 5 to 50° C., and still more preferably 10 to 20° C. A reaction time upon reaction (a) above is preferably 0.5 to 48 hours, more preferably 1 to 36 hours, and still more preferably 2 to 12 hours.

A solvent used in the reaction of (a) above includes aprotic polar solvents such as tetrahydrofuran, monoglyme, diglyme, triglyme, tetraglyme, acetonitrile, dimethylformamide, dimethylacetamide, methylpyrrolidone, dimethylethyleneurea, tetramethylurea, dimethylsulfoxide and sulfolane, or two-phase solvents of a protonic polar solvent such as water and a water-insoluble solvent such as dichloromethane, toluene and diethyl ether. Moreover, as the catalyst for the reaction in (a) above, a quaternary ammonium halide such as benzyltriethylammonium chloride, a quaternary phosphonium halide, a crown ether or the like can be used.

The method for producing a fluorinated pyrimidine compound of another embodiment includes:

(b) reacting a fluoroisobutane derivative represented by the following general formula (4) with a compound represented by the following general formula (3a) or a salt thereof to obtain a fluorinated pyrimidine compound represented by the following general formula (1a), or reacting a fluoroisobutane derivative represented by the following general formula (4) with a compound represented by the following general formula (3b) or a salt thereof to obtain a fluorinated pyrimidine compound represented by the following general formula (1b):

[Formula 12]

(4)

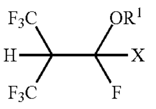

(3a)

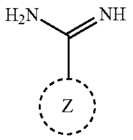

(1a)

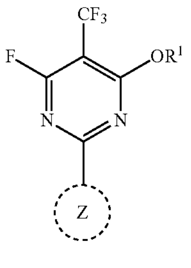

-continued (4)

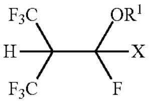

(3b)

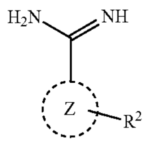

(1b)

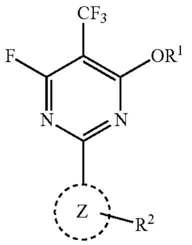

wherein $R^1$ represents a hydrocarbon group having 1 to 12 carbon atoms, $R^2$ represents a halogen atom, a hydrocarbon group having 1 to 10 carbon atoms, $—C_nF_{2n+1}$ where n is an integer of 1 to 10, a nitro group, a boronic acid group, a cyano group, $—OA^1$, $—O_1SO_mA^1$ where 1 is an integer of 0 to 1 and m is an integer of 0 to 3, $—NA^1A^2$, $—O_1COOA^1$ where 1 is an integer of 0 to 1, or $—O_1CONA^1A^2$ where 1 is an integer of 0 to 1, $A^1$ and $A^2$ each independently represent a hydrogen atom or a hydrocarbon group having 1 to 10 carbon atoms, $A^1$ and $A^2$ may be bonded to form a ring structure, and when a plurality of $R^2$ is present, the plurality of $R^2$ may be the same or different from each other, a ring Z is a 5-membered aromatic heterocyclic ring containing one oxygen atom and one or more nitrogen atoms, and X represents a halogen atom, a cyano group, $—OA^3$, $—NA^3A^4$, $—OCOOA^3$, $—OCONA^3A^4$, or $—O_1SO_mA^5$ where 1 is an integer of 0 to 1 and m is an integer of 0 to 3, $A^3$ and $A^4$ each independently represent a hydrocarbon group having 1 to 10 carbon atoms, $A^3$ and $A^4$ may be bonded to form a ring structure, and $A^5$ represents a hydrogen atom or a hydrocarbon group having 1 to 10 carbon atoms.

$R^1$, $R^2$, $A^1$, $A^2$, and the ring Z in the compounds of the general formulae (3a), (3b), and (4) in step (b) above can be specifically the same as $R^1$, $R^2$, $A^1$, $A^2$, and the ring Z in the compounds of the general formulae (1a) and (1b). Examples of the ring Z can include groups having structures represented by the following formulae (c1) to (c14). The structures of the following formulae (c1) to (c14) may be further bonded with $R^2$ as a substituent.

[Formula 13]

(c1)

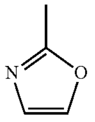

-continued (c2)

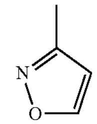

(c3)

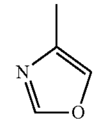

(c4)

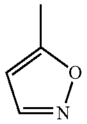

(c5)

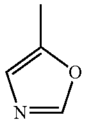

(c6)

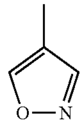

(c7)

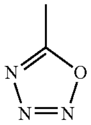

(c8)

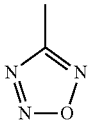

(c9)

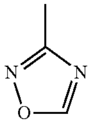

(c10)

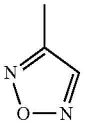

(c11)

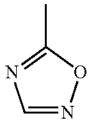

(c12)

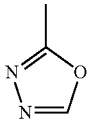

-continued (c13)

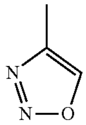

(c14)

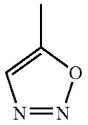

$A^3$ and $A^4$ in $—OA^3$, $—NA^3A^4$, $—OCOOA^3$, and $—OCONA^3A^4$, which are X in the compound of the general formula (4) in step (b) above, each independently represent a hydrocarbon group having 1 to 10 carbon atoms, and $A^3$ and $A^4$ may be bonded to form a ring structure. Examples of groups of the ring structure formed by bonding of $A^3$ and $A^4$ in $—NA^3A^4$ and $—NA^3A^4$ included in $—OCONA^3A^4$ can include a pyrrolidinyl group, a piperidinyl group, and a morpholinyl group. $A^3$ and $A^4$ can also be, for example, hydrocarbon groups having 1 to 10 carbon atoms in $R^1$ described above. $A^5$ in $—O_lSO_mA^5$ where l is an integer of 0 to 1 and m is an integer of 0 to 3, which is X in the compound of the general formula (4) in step (b) above, represents a hydrogen atom or a hydrocarbon group having 1 to 10 carbon atoms. For example, $A^5$ can be a hydrocarbon group having 1 to 10 carbon atoms in $R^1$ described above.

$R^1$ in the above general formulae (1a), (1b) and (4) preferably represents an alkyl group having 1 to 10 carbon atoms.

A reaction of (b) above between the fluoroisobutane derivative represented by the general formula (4) and the compound represented by the general formula (3a) or (3b) is represented by the following reaction formula (B).

[Formula 14]

(B)

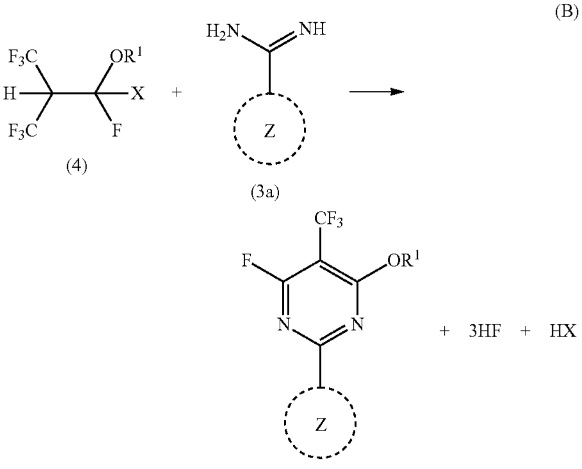

(4) (3a) (1a)

(B)

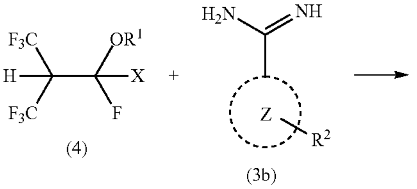

(4) (3b)

-continued

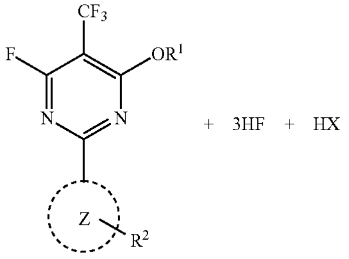

(1b)

In the reaction formula (B), the compounds of the general formulae (3a) and (3b) each may be in the form of salts. Examples of the compounds of the general formulae (3a) and (3b) in the form of salts include a compound in a form of at least one moiety of the amino moiety (—$NH_2$) and the imino moiety (═NH) constituting the amidino group of the compounds of the general formulae (3a) and (3b), being cationized to (—$NH_3^+$) and (═$NH_2^+$) respectively to form a salt with the counterion. The counterion is not particularly limited as long as it is a monovalent anion, and includes, for example, halide ions such as $F^-$, $Cl^-$, $Br^-$ and $I^-$.

In the method for producing a fluorinated pyrimidine compound of the other embodiment, for example, the reaction of (B) above can be carried out in one step. Therefore, the fluorinated pyrimidine compounds of the above general formula (1a) or (1b) can be easily obtained. In the reaction of (b) above, a cyclic pyrimidine structure is formed between the fluoroisobutane derivative and the amidino group of the compound of the general formula (3a) or (3b). At the 2-position of the pyrimidine structure, a group derived from the ring structure Z in the compound of the general formula (3a) or (3b) is located. Further, —$OR^1$, $CF_3$ and F derived from the fluoroisobutane derivative are located at the 4-position, 5-position and 6-position of the pyrimidine structure, respectively.

A reaction temperature upon reaction (b) above is preferably 0 to 100° C., more preferably 5 to 50° C., and still more preferably 10 to 20° C. A reaction time upon reaction (b) above is preferably 0.5 to 48 hours, more preferably 1 to 36 hours, and still more preferably 2 to 12 hours. In the reaction of (b) above, the same hydrogen halide scavenger as in (a) above can be used.

A solvent used in the reaction of (b) above includes aprotic polar solvents such as tetrahydrofuran, monoglyme, diglyme, triglyme, tetraglyme, acetonitrile, dimethylformamide, dimethylacetamide, methylpyrrolidone, dimethylethyleneurea, tetramethylurea, dimethylsulfoxide and sulfolane, or two-phase solvents of a protonic polar solvent such as water and a water-insoluble solvent such as dichloromethane, toluene and diethyl ether. Moreover, as a catalyst for the reaction of (b) above, quaternary ammonium halides such as benzyltriethylammonium chloride, a quaternary phosphonium halide and crown ether can be used.

Although the embodiments of the present disclosure have been described above, the present disclosure is not limited to the aforementioned embodiments, and includes all aspects included in the concept and claims of the present disclosure, and can be variously modified within the scope of the present disclosure.

EXAMPLES

Next, Examples will be described in order to further clarify an effect of the present disclosure, but the present disclosure is not limited to these Examples.

Example 1

Production of 6-fluoro-4-methoxy-2-(5-oxazolyl)-5-(trifluoromethyl)pyrimidine 0.8 g (4.9 mmol) of 5-oxazolecarboximidamide hydrochloride was dissolved in 50 ml of acetonitrile to make an acetonitrile solution. 1.2 g (5.7 mmol) of 1,3,3,3-tetrafluoro-1-methoxy-2-(trifluoromethyl)-1-propene and 3.3 g (25.5 mmol) of diisopropylethylamine were added into the acetonitrile solution, the mixture was stirred at room temperature for 19.1 hours, and the reaction solution was then purified by a column to obtain 0.4 g (1.5 mmol) of the compound represented by the following formula (5) (chemical formula: $C_9H_5F_4N_3O_2$, molecular weight: 263.15 g/mol). The isolated yield of the obtained compound was 31.1%.

[Formula 15]

(5)

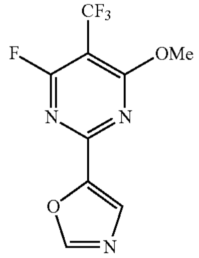

The analysis results of the obtained compound were as follows.

Mass Spectrum (APCI, m/z): 263.4 ($[M]^+$)

$^1H$-NMR (400 MHz, $CDCl_3$) δ ppm: 8.10 (s, 1H), 8.03 (s, 1H), 4.22 (s, 3H)

Example 2

Production of 6-fluoro-4-methoxy-2-(3-(5-methylisoxazolyl))-5-(trifluoromethyl)pyrimidine Under ice-water cooling, 0.5 g (3.1 mmol) of 3-amidino-5-methylisoxazole hydrochloride was dissolved in 10 g of acetonitrile, and 0.8 g (3.6 mmol) of 1,3,3,3-tetrafluoro-1-methoxy-2-(trifluoromethyl)-1-propene was added dropwise. Subsequently, a mixed solution of 2.1 g (16.1 mmol) of diisopropylethylamine and 5 g of acetonitrile was added dropwise, and the temperature was raised to room temperature. After stirring for 16 hours, the resulting reaction solution was purified by a column to obtain 0.3 g (1.2 mmol) of the compound represented by the following formula (6) (chemical formula: $C_{10}H_7F_4N_3O_2$, molecular weight: 277.18 g/mol). The isolated yield of the obtained compound was 40%.

[Formula 16]

(6)

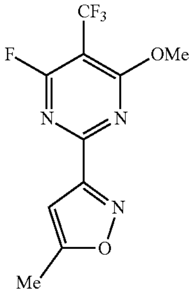

The analysis results of the obtained compound were as follows.

Mass Spectrum (APCI, m/z): 277.5 ($[M]^+$)

$^1$H-NMR (400 MHz, $CDCl_3$) δ ppm: 6.69 (s, 1H), 4.27 (s, 3H), 2.56 (s, 3H)

Example 3

Production of 6-fluoro-4-methoxy-2-(2-(1,3,4-oxadiazolyl))-5-(trifluoromethyl)pyrimidine Under ice-water cooling, 0.3 g (2.0 mmol) of 2-amidino-1,3,4-oxadiazole hydrochloride was dissolved in 8 g of acetonitrile, and 0.5 g (2.3 mmol) of 1,3,3,3-tetrafluoro-1-methoxy-2-(trifluoromethyl)-1-propene was added dropwise. Subsequently, a mixed solution of 1.3 g (10 mmol) of diisopropylethylamine and 5 g of acetonitrile was added dropwise, and the temperature was raised to room temperature. After stirring for 16 hours, the resulting reaction solution was purified by a column to obtain 0.1 g (0.4 mmol) of the compound represented by the following formula (7) (chemical formula: $C_8H_4F_4N_4O_2$, molecular weight: 264.14 g/mol). The yield of the obtained compound was 22%.

[Formula 17]

(7)

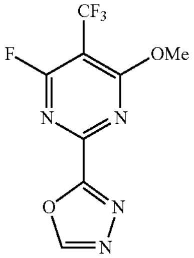

The analysis results of the obtained compound were as follows.

Mass Spectrum (APCI, m/z): 264.3 ($[M]^+$)

Example 4

Production of 6-fluoro-4-methoxy-2-(5-oxazolyl)-5-(trifluoromethyl)pyrimidine Using 1,1,1,3,3-pentafluoro-3-methoxy-2-(trifluoromethyl)-propane instead of 1,3,3,3-tetrafluoro-1-methoxy-2-(trifluoromethyl)-1-propene of Example 1

Under ice-water cooling, 0.8 g (4.9 mmol) of 5-oxazolecarboximidamide hydrochloride was dissolved in 20 g of acetonitrile, and 1.3 g (5.6 mmol) of 1,1,1,3,3-pentafluoro-3-methoxy-2-(trifluoromethyl)-propane was added dropwise. Subsequently, a mixed solution of 4.1 g (32 mmol) of diisopropylethylamine and 10 g of acetonitrile was added dropwise and the temperature was raised to room temperature. After about 16 hours, the contents were subjected to column purification. The analysis results of the obtained compound were the same as those of the product of Example 1.

Example 5

Production of 6-fluoro-4-methoxy-2-(3-(5-methylisoxazolyl))-5-(trifluoromethyl)pyrimidine using 1,1,1,3,3-pentafluoro-3-methoxy-2-(trifluoromethyl)-propane instead of 1,3,3,3-tetrafluoro-1-methoxy-2-(trifluoromethyl)-1-propene of Example 2

Under ice-water cooling, 0.5 g (3.1 mmol) of 3-amidino-5-methylisoxazole hydrochloride was dissolved in 10 g of acetonitrile, and 0.8 g (3.6 mmol) of 1,1,1,3,3-pentafluoro-3-methoxy-2-(trifluoromethyl)-propane was added dropwise. Subsequently, a mixed solution of 2.6 g (20 mmol) of diisopropylethylamine and 10 g of acetonitrile was added dropwise and the temperature was raised to room temperature. After about 16 hours, the contents were subjected to column purification. The analysis results of the obtained compound were the same as those of the product of Example 2.

Example 6

Production of 2-(4-(3-ethyl-5-methylisoxazolyl))-6-fluoro-4-methoxy-5-(trifluoromethyl)pyrimidine Under ice-water cooling, 0.3 g (1.5 mmol) of 4-amidino-3-ethyl-5-methylisoxazole hydrochloride was dissolved in 15 g of acetonitrile, and 0.4 g (1.7 mmol) of 1,3,3,3-tetrafluoro-1-methoxy-2-(trifluoromethyl)-1-propene was added dropwise. Subsequently, a mixed solution of 1.0 g (7.8 mmol) of diisopropylethylamine and 5 g of acetonitrile was added dropwise and the temperature was raised to room temperature. After stirring for 16 hours, the resulting reaction solution was purified by a column to obtain 0.3 g (1.1 mmol) of the compound represented by the following formula (8) (chemical formula: $C_{12}H_{11}F_4N_3O_2$, molecular weight: 305.23 g/mol). The isolated yield of the obtained compound was 74%.

[Formula 18]

(8)

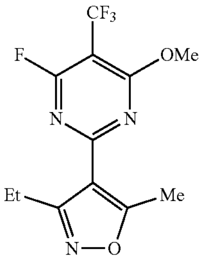

The analysis results of the obtained compound were as follows.

Mass Spectrum (APCI, m/z): 305.6 ([M]$^-$)

$^1$H-NMR (400 MHz, $CDCl_3$) δ ppm: 4.17 (s, 3H), 3.1 (q, 2H), 2.84 (s, 3H), 1.34 (t, 3H)

Example 7

Production of 6-fluoro-4-methoxy-2-(3-isoxazolyl)-5-(trifluoromethyl)pyrimidine 0.7 g (4.4 mmol) of 3-isoxazolecarboximidamide hydrochloride was dissolved in 44 ml of acetonitrile, 1.1 g (5.2 mmol) of 1,3,3,3-tetrafluoro-1-methoxy-2-(trifluoromethyl)-1-propene and 3.0 g (23.2 mmol) of diisopropylethylamine were added and stirred at room temperature for 16.3 hours, and the reaction solution was then purified by a column to obtain 0.5 g (1.7 mmol) of the compound represented by the following formula (9) (chemical formula: $C_9H_5F_4N_3O_2$, molecular weight: 263.15 g/mol). The isolated yield of the obtained compound was 39.3%.

[Formula 19]

(9)

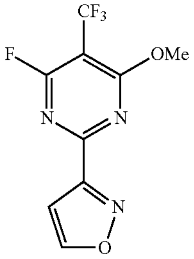

The analysis results of the obtained compound were as follows.

Mass Spectrum (APCI, m/z): 264.1 ([M+H]$^+$)

$^1$H-NMR (400 MHz, $CDCl_3$) δ ppm: 8.59 (d, J=1.5 Hz, 1H), 7.04 (d, J=1.8 Hz, 1H), 4.26 (s, 3H)

Example 8

Production of 6-fluoro-4-methoxy-2-(5-isoxazolyl)-5-(trifluoromethyl)pyrimidine 0.7 g (3.1 mmol) of 5-isoxazolecarboximidamide hydrochloride was dissolved in 31 ml of acetonitrile, 1.1 g (5.2 mmol) of 1,3,3,3-tetrafluoro-1-methoxy-2-(trifluoromethyl)-1-propene and 2.1 g (16.2 mmol) of diisopropylethylamine were added and stirred at room temperature for 15.3 hours, and the reaction solution was then purified by a column to obtain 0.1 g (0.3 mmol) of the compound represented by the following formula (10) (chemical formula: $C_9H_5F_4N_3O_2$, molecular weight: 263.15 g/mol). The isolated yield of the obtained compound was 9.9%.

[Formula 20]

(10)

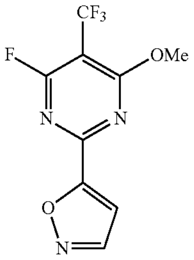

The analysis results of the obtained compound were as follows.

Mass Spectrum (APCI, m/z): 264.1 ([M+H]$^+$)

$^1$H-NMR (400 MHz, $CDCl_3$) δ ppm: 8.44 (d, J=1.8 Hz, 1H), 7.19 (d, J=1.8 Hz, 1H), 4.26 (s, 3H)

Example 9

Production of 6-fluoro-4-methoxy-2-(2-oxazolyl)-5-(trifluoromethyl)pyrimidine 0.8 g (5.2 mmol) of 2-oxazolecarboximidamide hydrochloride was dissolved in 52 ml of acetonitrile, 1.3 g (6.1 mmol) of 1,3,3,3-tetrafluoro-1-methoxy-2-(trifluoromethyl)-1-propene and 3.5 g (27.1 mmol) of diisopropylethylamine were added and stirred at room temperature for 18 hours, and the reaction solution was then purified by a column to obtain 0.7 g (2.6 mmol) of the compound represented by the following formula (11) (chemical formula: $C_9H_5F_4N_3O_2$, molecular weight: 263.15 g/mol). The isolated yield of the obtained compound was 50.5%.

[Formula 21]

(11)

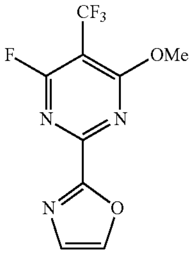

The analysis results of the obtained compound were as follows.

Mass Spectrum (APCI, m/z): 264.2 ([M+H]$^+$)

$^1$H-NMR (400 MHz, $CDCl_3$) δ ppm: 7.92 (s, 1H), 7.47 (s, 1H), 4.29 (s, 3H)

Example 10

Production of 6-fluoro-4-methoxy-2-(4-oxazolyl)-5-(trifluoromethyl)pyrimidine 0.5 g (3.5 mmol) of 1,3-oxazole-4-carboximidamide hydrochloride was dissolved in 30 ml of acetonitrile, 0.7 g (3.3 mmol) of 1,3,3,3-tetrafluoro-1-methoxy-2-(trifluoromethyl)-1-propene and 2.0 g (15.5 mmol) of diisopropylethylamine were added and stirred at room temperature for 18.2 hours, and the reaction solution was then purified by a column to obtain 0.4 g (1.4 mmol) of the compound represented by the following formula (12) (chemical formula: $C_9H_5F_4N_3O_2$, molecular weight: 263.15 g/mol). The isolated yield of the obtained compound was 41.7%.

[Formula 22]

(12)

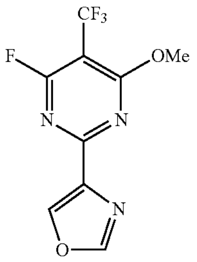

The analysis results of the obtained compound were as follows.

Mass Spectrum (APCI, m/z): 264.0 ($[M]^+$)

$^1$H-NMR (400 MHz, $CDCl_3$) δ ppm: 78.52 (d, J=0.9 Hz, 1H), 8.03 (d, J=0.9 Hz, 1H), 4.23 (8, 3H)

The invention claimed is:

1. A fluorinated pyrimidine compound represented by the following general formula (1a) or (1b):

[Formula 1]

(1a)

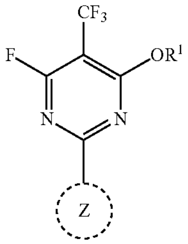

(1b)

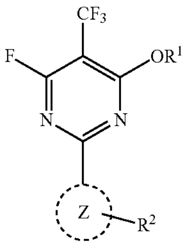

wherein $R^1$ represents a hydrocarbon group having 1 to 12 carbon atoms, $R^2$ represents a halogen atom, a hydrocarbon group having 1 to 10 carbon atoms, $—C_nF_{2n+1}$ where n is an integer of 1 to 10, a nitro group, a boronic acid group, a cyano group, $—OA^1$, $—O_lSO_mA^1$ where l is an integer of 0 to 1 and m is an integer of 0 to 3, $—NA^1A^2$, $—O_lCOOA^1$ where l is an integer of 0 to 1, or $—O_lCONA^1A^2$ where l is an integer of 0 to 1, $A^1$ and $A^2$ each independently represent a hydrogen atom or a hydrocarbon group having 1 to 10 carbon atoms, $A^1$ and $A^2$ may be bonded to form a ring structure, and when a plurality of $R^2$ is present, the plurality of $R^2$ is the same or different from each other, and a ring Z is a 5-membered aromatic heterocyclic ring containing one oxygen atom and one or more nitrogen atoms.

2. The fluorinated pyrimidine compound according to claim 1, wherein the ring Z has a structure of any one of the following formulae (c1) to (c14):

[Formula 2]

(c1)

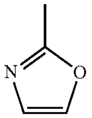

(c2)

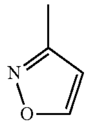

(c3)

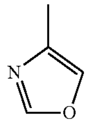

(c4)

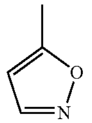

(c5)

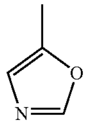

(c6)

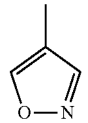

(c7)

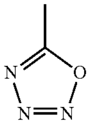

(c8)

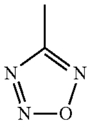

(c9)

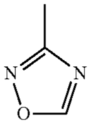

(c10)

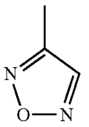

-continued (c11)

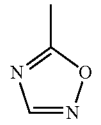

(c12)

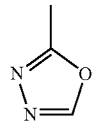

(c13)

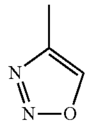

(c14)

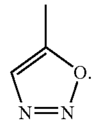

3. A method for producing a fluorinated pyrimidine compound, comprising:

reacting a fluoroisobutylene derivative represented by the following general formula (2) with a compound represented by the following general formula (3a) or a salt thereof to obtain a fluorinated pyrimidine compound represented by the following general formula (1a), or reacting a fluoroisobutylene derivative represented by the following general formula (2) with a compound represented by the following general formula (3b) or a salt thereof to obtain a fluorinated pyrimidine compound represented by the following general formula (1b):

[Formula 3]

(2)

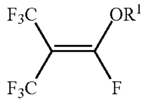

(3a)

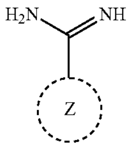

(1a)

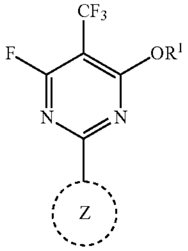

(2)

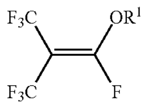

-continued (3b)

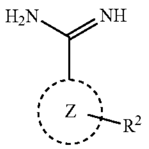

(1b)

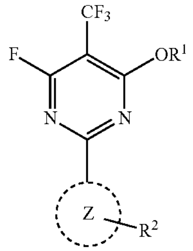

wherein $R^1$ represents a hydrocarbon group having 1 to 12 carbon atoms, $R^2$ represents a halogen atom, a hydrocarbon group having 1 to 10 carbon atoms, $—C_nF_{2n+1}$ where n is an integer of 1 to 10, a nitro group, a boronic acid group, a cyano group, $—OA^1$, $—O_lSO_mA^1$ where l is an integer of 0 to 1 and m is an integer of 0 to 3, $—NA^1A^2$, $—O_lCOOA^1$ where l is an integer of 0 to 1, or $—O_lCONA^1A^2$ where l is an integer of 0 to 1, $A^1$ and $A^2$ each independently represent a hydrogen atom or a hydrocarbon group having 1 to 10 carbon atoms, $A^1$ and $A^2$ may be bonded to form a ring structure, and when a plurality of $R^2$ is present, the plurality of $R^2$ is the same or different from each other, and a ring Z is a 5-membered aromatic heterocyclic ring containing one oxygen atom and one or more nitrogen atoms.

4. A method for producing a fluorinated pyrimidine compound, comprising:

reacting a fluoroisobutane derivative represented by the following general formula (4) with a compound represented by the following general formula (3a) or a salt thereof to obtain a fluorinated pyrimidine compound represented by the following general formula (1a), or reacting a fluoroisobutane derivative represented by the following general formula (4) with a compound represented by the following general formula (3b) or a salt thereof to obtain a fluorinated pyrimidine compound represented by the following general formula (1b):

[Formula 4]

(4)

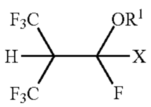

(3a)

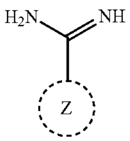

-continued

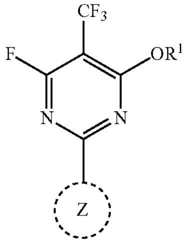

(1a)

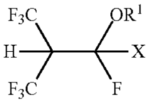

(4)

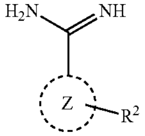

(3b)

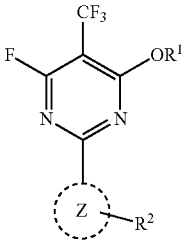

(1b)

wherein $R^1$ represents a hydrocarbon group having 1 to 12 carbon atoms, $R^2$ represents a halogen atom, a hydrocarbon group having 1 to 10 carbon atoms, $—C_nF_{2n+1}$ where n is an integer of 1 to 10, a nitro group, a boronic acid group, a cyano group, $—OA^1$, $—O_lSO_mA^1$ where l is an integer of 0 to 1 and m is an integer of 0 to 3, $—NA^1A^2$, $—O_lCOOA^1$ where l is an integer of 0 to 1, or $—O_lCONA^1A^2$ where l is an integer of 0 to 1, $A^1$ and $A^2$ each independently represent a hydrogen atom or a hydrocarbon group having 1 to 10 carbon atoms, $A^1$ and $A^2$ may be bonded to form a ring structure, and when a plurality of $R^2$ is present, the plurality of $R^2$ is the same or different from each other, a ring Z is a 5-membered aromatic heterocyclic ring containing one oxygen atom and one or more nitrogen atoms, and X represents a halogen atom, a cyano group, $—OA^3$, $—NA^3A^4$, $—OCOOA^3$, $—OCONA^3A^4$, or $—O_lSO_mA^5$ where l is an integer of 0 to 1 and m is an integer of 0 to 3, $A^3$ and $A^4$ each independently represent a hydrocarbon group having 1 to 10 carbon atoms, $A^3$ and $A^4$ may be bonded to form a ring structure, and $A^5$ represents a hydrogen atom or a hydrocarbon group having 1 to 10 carbon atoms.

5. The method for producing a fluorinated pyrimidine compound according to claim 3, wherein the ring Z has a structure of any one of the following formulae (c1) to (c14):

[Formula 5]

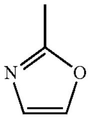

(c1)

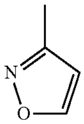

(c2)

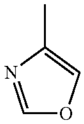

(c3)

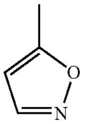

(c4)

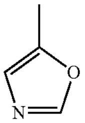

(c5)

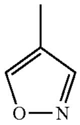

(c6)

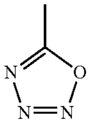

(c7)

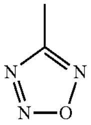

(c8)

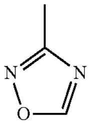

(c9)

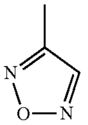

(c10)

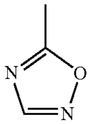

(c11)

-continued
(c12)
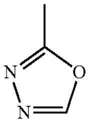
(c13)
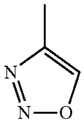
(c14)
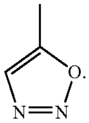
6. The method for producing a fluorinated pyrimidine compound according to claim 4, wherein the ring Z has a structure of any one of the following formulae (c1) to (c14):
[Formula 6]
(c1)
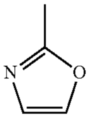
(c2)
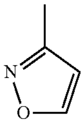
(c3)
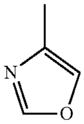
(c4)
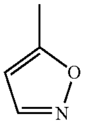
(c5)
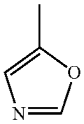
-continued
(c6)
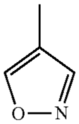
(c7)
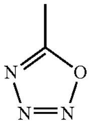
(c8)
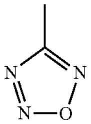
(c9)
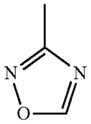
(c10)
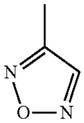
(c11)
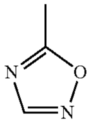
(c12)
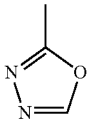
(c13)
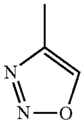
(c14)
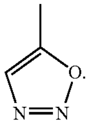
* * * * *